(12) United States Patent
Yamamoto et al.

(10) Patent No.: US 9,034,261 B2
(45) Date of Patent: May 19, 2015

(54) SYSTEM AND METHOD FOR DEPOSITING PARTICLES ON A DISC

(75) Inventors: Masanobu Yamamoto, Yokohama (JP); Michael D. Zordan, Champaign, IL (US); Gary P. Durack, Urbana, IL (US); Larry W. Arnold, Snow Camp, NC (US)

(73) Assignees: Sony Corporation, Tokyo (JP); Sony Corporation of America, New York, NY (US)

( * ) Notice: Subject to any disclaimer, the term of this patent is extended or adjusted under 35 U.S.C. 154(b) by 13 days.

(21) Appl. No.: 13/611,853

(22) Filed: Sep. 12, 2012

(65) Prior Publication Data
US 2014/0072997 A1 Mar. 13, 2014

(51) Int. Cl.
*G01N 33/487* (2006.01)
*G01N 33/49* (2006.01)

(52) U.S. Cl.
CPC ...... *G01N 33/48771* (2013.01); *G01N 33/4915* (2013.01)

(58) Field of Classification Search
None
See application file for complete search history.

(56) References Cited

U.S. PATENT DOCUMENTS

| 5,674,743 | A * | 10/1997 | Ulmer | 435/287.2 |
| 7,141,416 | B2 | 11/2006 | Krutzik | |
| 7,428,200 | B2 | 9/2008 | Coombs et al. | |
| 2003/0211637 | A1 * | 11/2003 | Schoeniger et al. | 436/523 |
| 2004/0038307 | A1 * | 2/2004 | Lee et al. | 435/7.1 |
| 2007/0059763 | A1 * | 3/2007 | Okano et al. | 435/7.1 |
| 2009/0032401 | A1 * | 2/2009 | Ronaghi et al. | 204/549 |
| 2009/0042739 | A1 * | 2/2009 | Okano et al. | 506/12 |
| 2010/0062415 | A1 * | 3/2010 | Schwoebel et al. | 435/5 |
| 2012/0241643 | A1 * | 9/2012 | Palmer et al. | 250/428 |
| 2014/0235468 | A1 * | 8/2014 | Cheng et al. | 506/9 |

FOREIGN PATENT DOCUMENTS

EP 1577010 A3 11/2005

OTHER PUBLICATIONS

Sundberg, et al., "Spinning Disk Platform for Microfluidic Digital Polymerase Chain Reaction", Analytical Chemistry, Feb. 15, 2010, pp. 1546-1550, vol. 82, No. 4, American Chemical Society.
Morais, et al., "DNA microarraying on compact disc surfaces. Application to the analysis of single nucleotide poly morphisms in Plum pox virus", Chemical Communications, May 2, 2006, pp. 2368-2370, RSC Publishing.
Varma, et al., "High-speed label-free detection by spinning-disk micro-interferometry", Biosensors and Bioelectronics, 2004, pp. 1371-1376.

* cited by examiner

*Primary Examiner* — Bao Thuy L Nguyen
*Assistant Examiner* — Gary E Hollinden
(74) *Attorney, Agent, or Firm* — Ice Miller LLP

(57) ABSTRACT

A system and method are disclosed in which particles sorted by a flow cytometer may be deposited directly into a deposition layer formed on the surface of an optical disc, and information regarding measurements made of the particle, as well as the storage location of the particle, can be written to the recording layer of the optical disc.

24 Claims, 6 Drawing Sheets

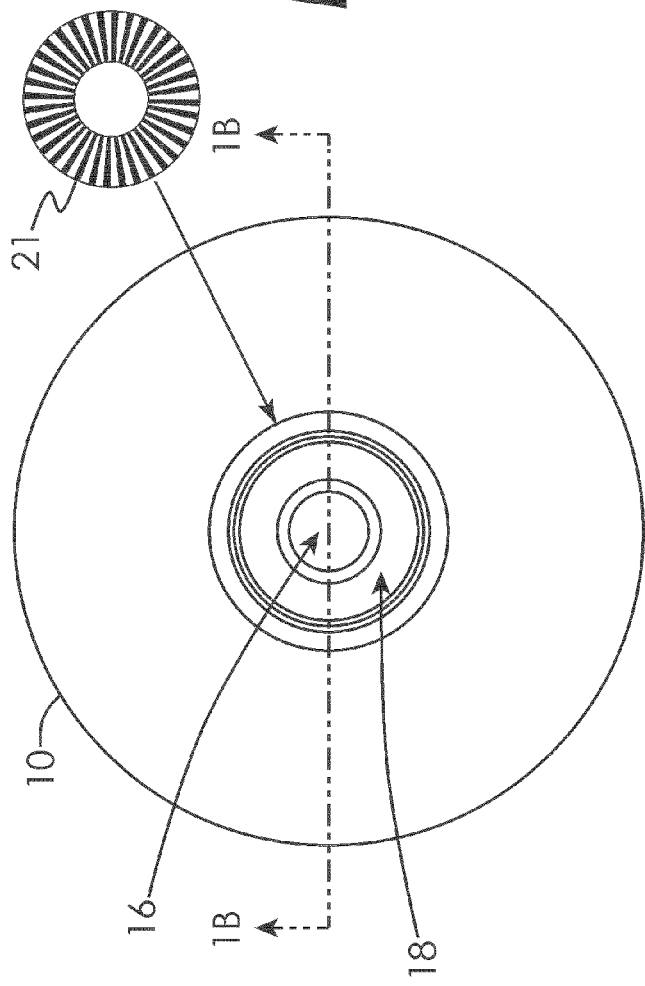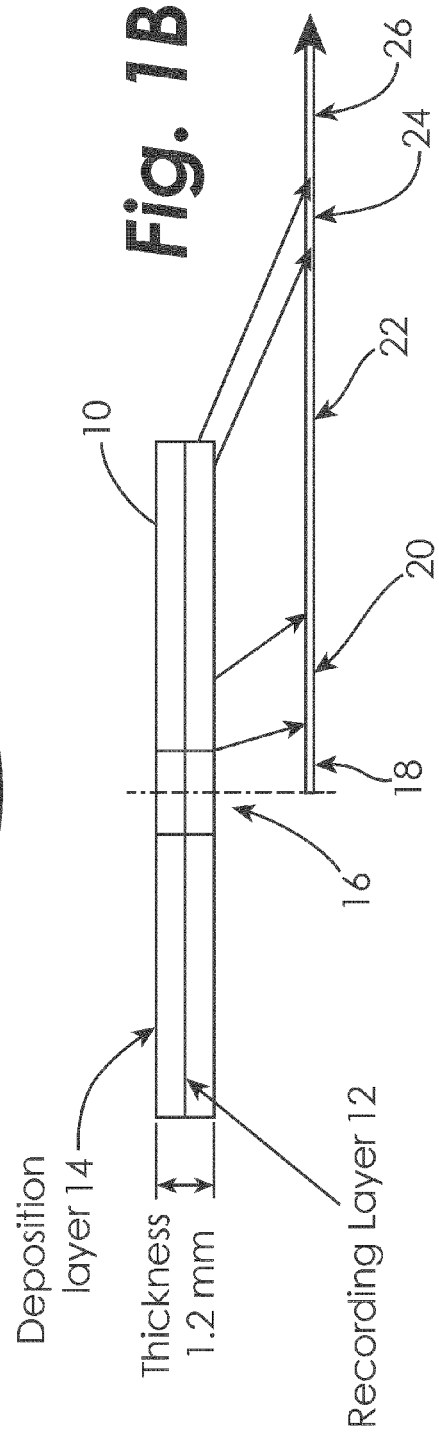
Fig. 1A
Fig. 1B

CLV Layout

CAV Layout

SYSTEM AND METHOD FOR DEPOSITING PARTICLES ON A DISC

TECHNICAL FIELD OF THE INVENTION

The present invention generally relates to particle measurement and storage and, more particularly, to a system and method for depositing particles on a disc after measurement of the particles.

BACKGROUND OF THE INVENTION

Although the concepts of the present disclosure will find application in use with a wide variety of particle measurement systems, these concepts are exemplarily illustrated herein by use with a flow cytometer. Flow cytometry-based cell sorting was first introduced to the research community more than 30 years ago. It is a technology that has been widely applied in many areas of life science research, serving as a critical tool for those working in fields such as genetics, immunology, molecular biology and environmental science. Unlike bulk cell separation techniques such as immuno-panning or magnetic column separation, flow cytometry-based cell sorting instruments measure, classify and then sort individual cells or particles (both terms are used herein interchangeably to refer to living or non-living (biological or non-biological) objects to be analyzed) serially at rates of several thousand cells per second or higher. This rapid "one-by-one" processing of single cells has made flow cytometry a unique and valuable tool for extracting highly pure sub-populations of cells from otherwise heterogeneous cell suspensions.

Cells targeted for sorting are usually labeled in some manner with a fluorescent material. The fluorescent probes bound to a cell emit fluorescent light as the cell passes through a tightly focused, high intensity, light beam (typically a laser beam, although other light sources can be used). A computer records emission intensities for each cell. These data are then used to classify each cell for specific sorting operations. Flow cytometry-based cell sorting has been successfully applied to hundreds of cell types, cell constituents and microorganisms, as well as many types of inorganic particles of comparable size.

Flow cytometers are also applied widely for rapidly analyzing heterogeneous cell suspensions to identify constituent sub-populations. Examples of the many applications where flow cytometry cell sorting is finding use include isolation of rare populations of immune system cells for AIDS research, isolation of genetically atypical cells for cancer research, isolation of specific chromosomes for genetic studies, and isolation of various species of microorganisms for environmental studies. For example, fluorescently labeled monoclonal antibodies are often used as "markers" to identify immune cells such as T lymphocytes and B lymphocytes, clinical laboratories routinely use this technology to count the number of "CD4 positive" T cells in HIV infected patients, and they also use this technology to identify cells associated with a variety of leukemia and lymphoma cancers.

Recently, two areas of interest are moving cell sorting towards clinical, patient care applications, rather than strictly research applications. First is the move away from chemical pharmaceutical development to the development of biopharmaceuticals. For example, many new cancer therapies utilize biological material. These include a class of antibody-based cancer therapeutics. Cytometry-based cell sorters can play a vital role in the identification, development, purification and, ultimately, production of these products.

Related to this is a move toward the use of cell replacement therapy for patient care. Much of the current interest in stem cells revolves around a new area of medicine often referred to as regenerative therapy or regenerative medicine. These therapies may often require that large numbers of relatively rare cells be isolated from patient tissue. For example, adult stem cells may be isolated from bone marrow and ultimately used as part of a re-infusion back into the patient from whom they were removed. Flow cytometry and cell sort are important tissue processing tools that enable delivery of such therapies.

There are two basic types of cell sorters in wide use today. They are the "droplet cell sorter" and the "fluid switching cell sorter." The droplet cell sorter utilizes micro-droplets as containers to transport selected cells to a collection vessel. The micro-droplets are formed by coupling ultrasonic energy to a jetting stream. Droplets containing cells selected for sorting are then electrostatically steered to the desired location. This is a very efficient process, currently allowing as many as 90,000 cells per second to be sorted from a single stream, limited primarily by the frequency of droplet generation and the time required for illumination.

A detailed description of a prior art flow cytometry system is given in United States Published Patent Application No. US 2005/0112541 A1 to Durack et al.

The second type of flow cytometry-based cell sorter is the fluid switching cell sorter. Most fluid switching cell sorters utilize a piezoelectric device to drive a mechanical system which diverts a segment of the flowing sample stream into a collection vessel. Compared to droplet cell sorters, fluid switching cell sorters have a lower maximum cell sorting rate due to the cycle time of the mechanical system used to divert the sample stream. This cycle time, the time between initial sample diversion and when stable non-sorted flow is restored, is typically significantly greater than the period of a droplet generator on a droplet cell sorter. This longer cycle time limits fluid switching cell sorters to processing rates of several hundred cells per second. For the same reason, the stream segment switched by a fluid cell sorter is usually at least ten times the volume of a single micro-drop from a droplet generator. This results in a correspondingly lower concentration of cells in the fluid switching sorter's collection vessel as compared to a droplet sorter's collection vessel.

When isolating cells of a particular type from a larger population, all cells of the particular type may be directed into the same collection vessel in order to create a greatly purified version of the original sample. In some applications, this type of collection is adequate as all that is required is to "reject" from the sample as much unwanted material as possible in order to increase its purity. In other applications, it may be desirable to isolate each of the identified target particles for further study or processing. A common prior art device that may lend itself to such storage is the so-called microwell plate or "microplate." A microplate is a flat plate with multiple "wells" used as small test tubes. The microplate has become a standard tool in analytical research and clinical diagnostic testing laboratories. A microplate typically has 6, 24, 96, 384 or even 1536 sample wells arranged in a 2:3 rectangular matrix. Each well of a microplate typically holds somewhere between tens of nanoliters to several milliliters of liquid. Microplates can be stored at low temperatures for long periods, may be heated to increase the rate of solvent evaporation from their wells and can even be sealed with foil or clear film. Today there are microplates for just about every application in life science research which involves filtration, separation, optical detection, storage, reaction mixing or cell culture, as well as many other disciplines.

Although the microplate has become a standard mechanism for storing and handling samples in life sciences laboratory work, their limited storage capacity compared to the number of cells that may be analyzed by a flow cytometer in a very short time makes them impractical for storing cells identified through flow cytometry. Improvements in flow cytometer sorter output storage technology are therefore still desired.

SUMMARY OF THE DISCLOSED EMBODIMENTS

The presently disclosed embodiments enable, for a flow cytometer cell sorter, the ability to accurately store a large quantity of sorted particles, together with measurement data associated with each sorted particle, on a single substrate for later retrieval and use.

The presently disclosed embodiments provide a system and method for depositing sorted particles onto an optical disc, and recording on the disc data regarding the location of each particle stored on the disc and the measurement data associated with the particle. In one embodiment, more than 60,000 particles may be deposited onto a single optical disc along with data relating to specific, individual stored particles.

In one embodiment, a system is disclosed, comprising: a flow cytometer having at least one droplet moving on a jetting axis; a deposition disc comprising a deposition layer; wherein the jetting axis intersects a portion of the deposition layer; and a rotational drive system coupled to the deposition disc for controlling angular motion of the deposition disc; wherein the at least one droplet may be deposited by the flow cytometer onto the deposition layer.

In one embodiment, a deposition disc is disclosed, comprising: a recording layer comprising a laser guiding groove and a recording dye; and a deposition layer having a droplet deposition feature formed therein.

In another embodiment, a system for use with a flow cytometer having at least one droplet moving on a jetting axis is disclosed, the system comprising: a deposition disc comprising: a deposition layer; and a recording layer; wherein the deposition layer is positioned adjacent the recording layer; wherein the jetting axis intersects a portion of the deposition layer; and wherein the at least one droplet may be deposited by the flow cytometer onto the deposition layer; a first laser producing first laser light; a second laser producing second laser light; a first optical path operative to guide a first axis of the first laser light to be coextensive with the jetting axis; a second optical path operative to guide a second axis of the second laser light to be coextensive with the jetting axis; a lens intersected by the jetting axis; wherein the lens focuses the first laser light on the recording layer; wherein the lens focuses the second laser light on the deposition layer; a photodetector system operative to simultaneously detect first laser light reflected from the recording layer and second laser light reflected from the deposition layer.

In yet another embodiment, a method of depositing droplets on a deposition disc is disclosed, comprising the steps of: a) flowing a droplet on a jetting axis of a flow cytometer; b) measuring with the flow cytometer measurement data relating to the droplet; c) depositing the droplet onto the deposition disc; d) sensing a location of the deposited droplet on the deposition disc; and e) recording on the deposition disc data relating to the location.

Other embodiments are also disclosed.

BRIEF DESCRIPTION OF THE DRAWINGS

FIG. 1A is a plan view an optical disc according to one embodiment of the present disclosure.

FIG. 1B is a cross-sectional view of the optical disc of FIG. 1A.

DETAILED DESCRIPTION OF THE DISCLOSED EMBODIMENTS

Figure 2:
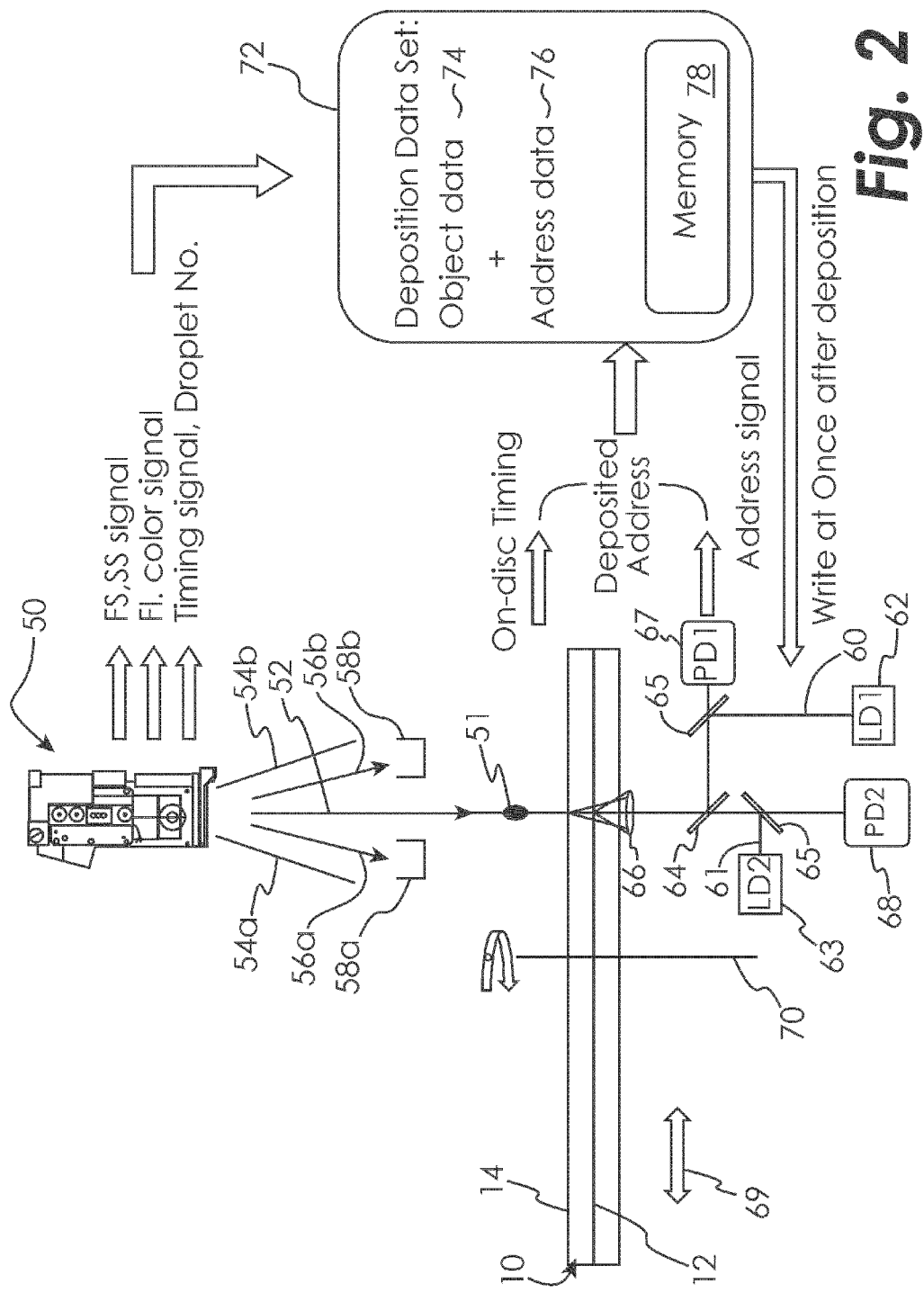
FIG. 2 is a schematic view of a deposition optical disc and flow cytometer according to one embodiment of the present disclosure.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Referring to FIGS. 1A-B, there is shown a plan view and a cross-sectional view of a recordable optical data disc indicated generally at 10, such a recordable digital versatile disc (DVD-R) or recordable Blu-ray Disc® (BD-R), to name just two non-limiting examples. The principles of the present disclosure will find application with any type of recordable optical disc, whether now known or hereafter developed. As shown in FIG. 1B, DVD-R discs 10 are composed of two 0.6 mm acrylic or polycarbonate substrates, bonded to one another with a UV-hardening resin. In the case of the Blu-ray Disc®, the cover layer is 0.1 mm thick and the supporting substrate is 1.1 mm thick, for a total thickness of 1.2 mm. The bottom recording layer 12 contains a laser guiding groove and is coated with the recording dye (such as azo, cyanine, or dipyrromethene to name just three examples—the type of recording medium used is not critical to the present invention) and a silver alloy or gold reflector. In some embodiments, more than one recording layer 12 may be present and all recording layers 12 may be read with the same laser, as is known in the art. The top layer 14 is an ungrooved 'dummy' disc to assure mechanical stability of the sandwich structure, and compatibility with the compact disc (CD) standard geometry which requires a total disc thickness of about 1.2 mm. The sandwich structure also helps protect the recording layer 12 from scratches with the thick 'dummy' disc, a problem with CDs, which lack that structure. In the presently disclosed embodiments, the top layer 14 is not a 'dummy' disc, but rather is modified to be used as a deposition layer for the storage of cells sorted using a flow cytometer, as will be described in greater detail hereinbelow.

The center of the disc 10 comprises a hole 16 (nominally 15 mm in diameter) used to mount the disc 10 to a drive mechanism. The outer edge of the hole 16 therefore has a radius of 7.5 mm from the center of the disc. From the edge of the center hole 16 to a point at a radius of 16.5 mm is the hub clamp area 18, used for securely clamping the disc 10 to the drive mechanism. A lead-in zone 20 containing information about the disc 10 starts at a radius of 22 mm. For example, a rotary encoder pattern 21 may be formed by groove diffraction grating. This allows the system to detect absolute angular position of the disc 10, as well as incremental angular position. The recordable data zone 22 starts at a radius of 24 mm and ends at a radius of 58 mm, where a lead-out zone 24 begins. Data zone 22 therefore comprises 8758.5 mm$^2$ onto which data may be recorded. The lead-out zone 24 marks the end of the data zone 22 and extends to a radius of 58.5 mm. Exterior to the lead-out zone 24 is a 1.5 mm radius blank area 26 to the edge of the disc 10.

Information may be written to and read from the recording layer 12 in the data zone 22 using an optical system positioned below the disc 10. The drive mechanism and optical system used with the disc 10 are discussed in greater detail hereinbelow. In current industry configurations, information is written to a DVD-R using 650 nm wavelength (red) laser diode light with a lens having a numerical aperture of 0.6, which produces a pit or recorded mark having a feature track pitch of 0.74 μm embossed into the recording layer 12, permitting a storage capacity of 4.7 GB of data to be recorded on the recording layer 12. By contrast, information is written to a BD-R using 405 nm wavelength (blue-violet) laser diode light with a lens having a numerical aperture of 0.85, which produces a pit or recorded mark having a feature track pitch of 0.32 μm embossed into the recording layer 12, permitting a storage capacity of 25 GB of data to be recorded on the recording layer 12.

In the embodiments disclosed herein, the deposition layer 14 is not configured as a 'dummy' disc as is the case with prior art DVDs and Blu-ray Discs®. Instead, in some embodiments the upper surface of the deposition layer 14 is impressed with a spiral groove in the same or similar configuration as the groove used in the recording layer 12. The configuration of such grooves as used in prior art devices are well known in the art. In the embodiments disclosed herein, droplets/cells may be deposited directly onto the deposition layer 14 after being sorted by the flow cytometer. In other embodiments, the upper surface of the deposition layer 14 is impressed with microwells arranged in radial lines extending between the inner and outer radii of the disc 10. In other embodiments, the deposition layer 14 is flay or substantially flat, with no surface features.

With reference now to FIG. 2, a flow cytometer is illustrated generally at 50. As is known in the art, the flow cytometer produces a series of droplets, many of which contain cells to be measured and sorted. Droplets that are desired to be kept may either be allowed to continue on their downward path or deflected to either side, and droplets that are not to be kept (waste) are routed in the opposite direction. In the embodiment illustrated in FIG. 2, the droplets desired to be kept are allowed to continue on the droplet jetting axis 52, while the other droplets are deflected by one or more electrically charged plates 54a, 54b onto trajectories 56a, 56b into waste repositories 58a, 58b. While the droplets on trajectories 56a, 56b are referred to herein as waste, it will be understood that they may also be separated out for further processing rather than being disposed of.

The droplets 51 that remain on the jetting axis 52 will be deposited onto the deposition layer 14 of a disc 10 positioned below the stream 52. Light 60 from laser diode one (LD1) 62 is reflected by beamsplitter prism 65 and dichroic mirror 64 and is focused onto the recording layer 12 of disc 10 by objective lens 66. In one embodiment, LD1 62 comprises a 650 nm laser diode. Light reflected from the recording layer 12 of disc 10 is reflected by the dichroic mirror 64, passes through the beamsplitter prism 65 and is sensed by a photodetector 67 to determine the read/write location corresponding to the droplet 51 on the recording layer 12.

Conventional DVD optical pick-up assemblies have the capablility to read CDs (cover 1.2 mm thick) and DVDs (cover 0.6 mm thick). The pick-up assembly includes two lasers (650 nm & 780 nm wavelengths), one objective lens (in which the effective NA is different for the 780 nm laser (NA-0.45) and the 650 nm laser (NA-0.60)), and one detection photodiode (multi-divided). The pick-up assembly first checks whether a CD or DVD is to be read, and then the appropriate CD or DVD optics function is operated to play back the contents of the disc. Thus, only one wavelength is used for read/write operations based on what type of disc is being used.

In the presently disclosed embodiments, both lasers/wavelengths are used simultaneously. Focusing, tracking, address/signal reading and data writing are executed by the 650 nm LD1 62. The 780 nm optics are used simultaneously in the presently disclosed embodiments for droplet detection on deposition layer 14 with same optical axis as the 650 nm laser, but with a different focus point on the layer 14 (due to the different numerical aperture of the lens 66 for the different wavelengths).

When a droplet 51 on jetting axis 52 is deposited onto the deposition layer 14, light 61 from laser diode two (LD2) 63 is reflected by beamsplitter 65 and passes through dichroic mirror 64 and is focused onto the deposition layer 14 by objective lens 66. In one embodiment, LD2 63 comprises a 780 nm laser diode. Light reflected from the deposition layer 14 passes through dichroic mirror 64 and beamsplitter 65 and is sensed by photodetector 68 to detect the droplet landing. Since PD1 67 is constantly reading the address on layer 12, the system can determine at what address the droplet 51 was deposited from the readings made simultaneously by the two photodetectors.

The normal configuration for prior art optical discs is to cause the disc to spin on a fixed spindle and to move the optical system radially to access all areas of the disc. In some of the embodiments disclosed herein, the optical system 60-68 remains stationary, with the axis of the light 60, 61 from both lasers aligned with the jetting axis 52 of the sorted droplets, while the disc 10 rotation spindle is moved horizontally, parallel to the marked axis 69. The disc 10 is rotated about its central axis 70 by means of an appropriate rotational drive system (not shown).

A deposition data set is assembled by a data processing device(s) 72 operatively coupled to the cytometer 50 and the optical system 60-68 for receipt of information therefrom. In this way, the data processing device 72 may assemble a deposition data set that includes object data 74 (e.g. measurement information) from the cytometer 50 and address data 76 (e.g. where on the disc 10 the sorted droplet was deposited) from the optical system 60-68. All or part of the deposition data set may be optionally temporarily stored in memory 78 associated with the data processing device 72. The deposition data set is written to the recording layer 12 by the optical system 60-68. In this way, the disc 10 contains both the cell samples deposited thereon, as well as data that contains measurement information about each cell, coupled with address information revealing where on the disc 10 the sample cell may be found. By way of non-limiting example only, the object data 74 obtained from the cytometer 50 may include the flourescence signal, scatter signal, flourescence marker signal, timing signal, droplet number, or other desired information about the sample.

Figure 3A:
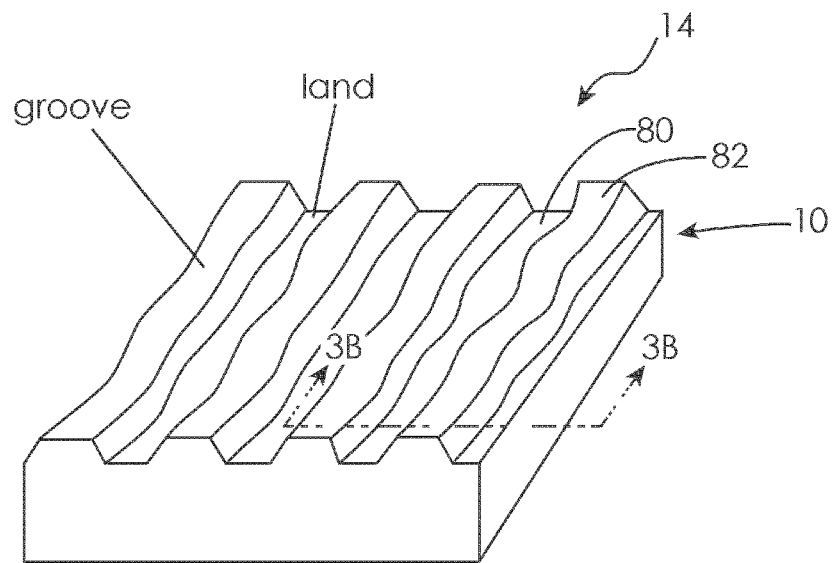
FIG. 3A is a partial cross-sectional view of an optical disc according to one embodiment of the present disclosure.

Referring now to FIG. 3A, there is illustrated a perspective view of a portion of one embodiment of disc 10 deposition layer 14, showing several sections of a groove 80 separated by land sections 82. The patterning of the deposition layer 14 may be accomplished by any desired process, such as disc mastering, mechanical processing, semiconductor processing, or three-dimensional micro-lithography, just to name a few non-limiting examples. The deposition layer 14 may also include a surface treatment to facilitate the deposition and/or storage of the deposited cells, such as covering the deposition layer (or at least the groove 80 surfaces) with a primer, a hydrophobic coating, or a hydrophilic coating, just to name a few non-limiting examples. Such surface treatment may be accomplished by ink jet plotting, spin coating, or any other appropriate process. In other embodiments, wells may be formed into the deposition layer 14, with or without the presence of the groove 80. Deposited cells may be placed into individual wells. In other embodiments, the deposition layer 14 may be substantially flat, with no surface features.

Figure 3B:
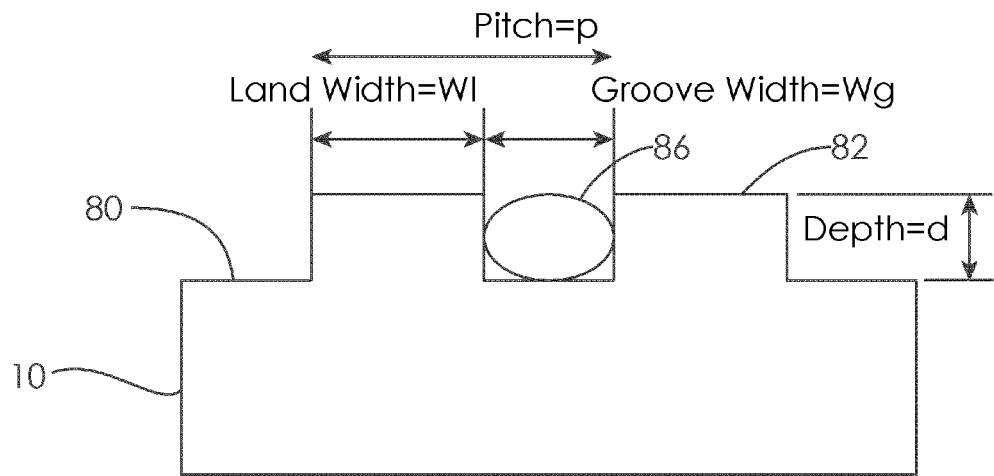
FIG. 3B is a partial cross-sectional view of the optical disc of FIG. 3A.

Referring now to FIG. 3B, a cross-sectional view of the disc 10 is shown, defining deposition layer 14 feature measurements p (pitch), Wl (Land Width), Wg (Groove Width) and d (groove depth). A droplet 86 is shown residing in the groove 80 after deposition. Some of the relevant dimensions of the deposition layer 14 and times for the deposition process can be estimated in one embodiment as follows:

Droplet 86 volume is: $4\pi r^3/3$
r~50 μm (depending on surface tension)
therefore droplet 86 volume=~52 nl.
Wg is desired to be >Disc Radial Runout+Deposition Accuracy+Droplet Radius=~50 μm+~100 μm+50 μm=~200 μm
d: equal to droplet radius ~50 μm
p: >2×Wg=400 μm=0.4 mm
L: total length of groove=$\pi/p\times(ro^2-ri^2)$=3.14/0.4 (58*58−24*24)=21,885 mm
V: CLV (Constant Linear Velocity) Scanning velocity=3.5 m/sec
T: Deposition time in groove=L/V=6.25 sec/disc
DF: Droplet Rate=40 kHz (frequency with which droplets 86 are created by the cytometer 50)
EF: Event Rate=10 kHz (frequency at which sorted droplets are expected to be deposited onto the deposition layer 14)
Deposition distance in groove: V/EF=3.5 m/10 k=350 μm/sample
Total Number of Depositions: EF*T=10 k×6.25 sec=62.25 k samples/disc
Sample data: 2080 bit/sample=260 Byte/sample
Address data: 40 Byte
Data/sample: 300 Byte
Total Data to Record: 18.765 MB
which is well within the storage capacity of the disc. Thus, even larger amounts of data could be stored for each deposition sample, and/or more deposition samples may be stored on the disc 10 using different disc, droplet and/or scanning parameters.

Figure 4:
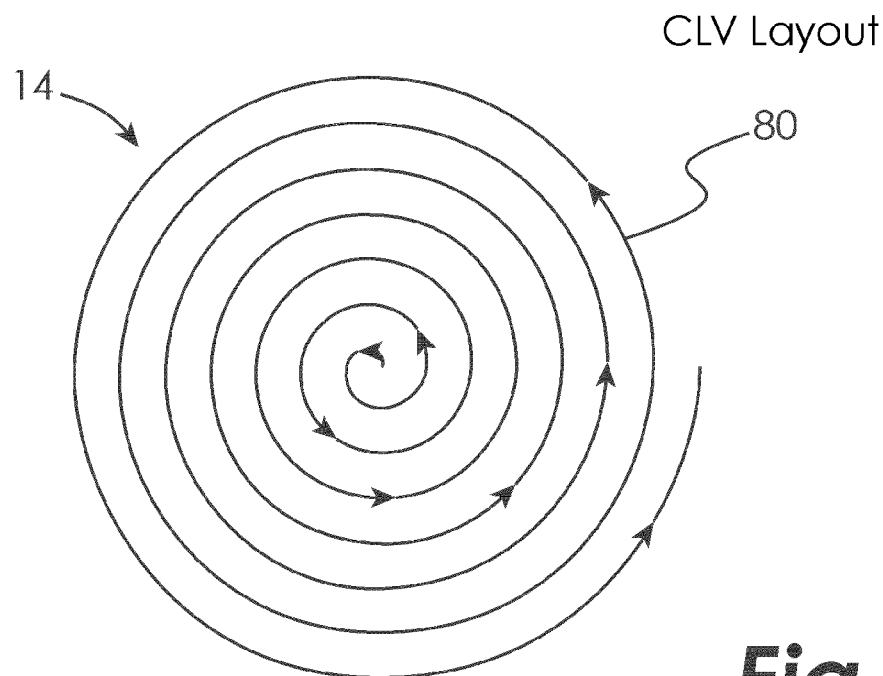
FIG. 4 is a schematic plan view of a first embodiment optical disc of the present disclosure.

Referring now to FIG. 4, the single groove 80 of a disc 10 is shown schematically. It can be seen that the groove 80 begins at the inner radius and spirals outwardly at a constant pitch until it reaches the outer radius. In this configuration, the disc 10 is maintained at a constant linear velocity (CLV), meaning that the disc 10 angular velocity (rpm) is decreased as the optical axis is moved toward the outer radius, thereby keeping the speed of the groove moving past the optical axis constant. The number of droplets 86 that may be deposited onto the deposition layer 14 in this arrangement varies by the pitch of the groove.

Microwell pitch: p
Total scanning length: L
Number of microwells: N=L/p
Diameter of microwell: p/2
The number of microwells that may be accommodated on the disc 10 may therefore be summarized as follows:

| p mm | well dia | L mm | N well | T scan sec |
|---|---|---|---|---|
| 1.0 | 0.50 | 8,754 | 8,754 | 2.50 |
| 0.9 | 0.45 | 9,727 | 10,808 | 2.78 |
| 0.8 | 0.40 | 10,943 | 13,679 | 3.13 |
| 0.7 | 0.35 | 12,506 | 17,866 | 3.57 |
| 0.6 | 0.30 | 14,591 | 24,318 | 4.17 |
| 0.5 | 0.25 | 17,509 | 35,017 | 5.00 |
| 0.4 | 0.20 | 21,886 | 54,715 | 6.25 |
| 0.3 | 0.15 | 29,181 | 97,270 | 8.34 |
| 0.2 | 0.10 | 43,772 | 218,858 | 12.51 |
| 0.1 | 0.05 | 87,543 | 875,432 | 25.01 |

Figure 5:
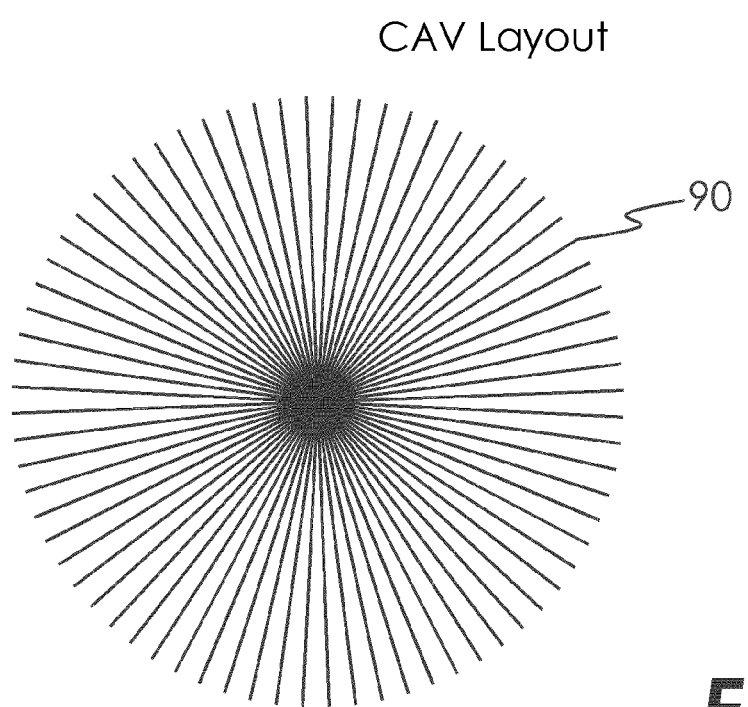
FIG. 5 is a schematic plan view of a second embodiment optical disc of the present disclosure.

Referring now to FIG. 5, another embodiment for arrangement of the deposition layer 14 on the disc 10 is illustrated. Rather than providing a single spiral groove 80 on the disc 10, the embodiment of FIG. 5 utilizes microwells that are formed on radial lines 90. With this arrangement, the disk can be maintained at a constant angular velocity (CAV) or step and repeat movement since the disc is capturing droplets in the microwell at an arbitrary on-disc timing. The number of droplets 86 that may be deposited onto the deposition layer 14 in this arrangement varies by the pitch of the microwells, but the total number of microwells that may be formed on the disc 10 is less for any given pitch when compared to the CLV embodiment of FIG. 4 that utilizes a groove.

Micro-well pitch: p
Length of inner radius: $l=2\pi ri$
No. of wells at inner radius: n=l/p
Number of micro-wells on disc: N=n×(ro−ri)/p
Diameter of micro-well: p/2
The number of microwells that may be accommodated on the disc 10 may therefore be summarized as follows:

| p mm | well dia | n | N |
|---|---|---|---|
| 1.00 | 0.50 | 151 | 5,127 |
| 0.90 | 0.45 | 168 | 6,330 |
| 0.80 | 0.40 | 189 | 8,011 |
| 0.70 | 0.35 | 215 | 10,464 |
| 0.60 | 0.30 | 251 | 14,242 |
| 0.50 | 0.25 | 302 | 20,509 |
| 0.40 | 0.20 | 377 | 32,045 |
| 0.30 | 0.15 | 503 | 56,969 |
| 0.20 | 0.10 | 754 | 128,180 |
| 0.10 | 0.05 | 1,508 | 512,720 |

Figure 6:
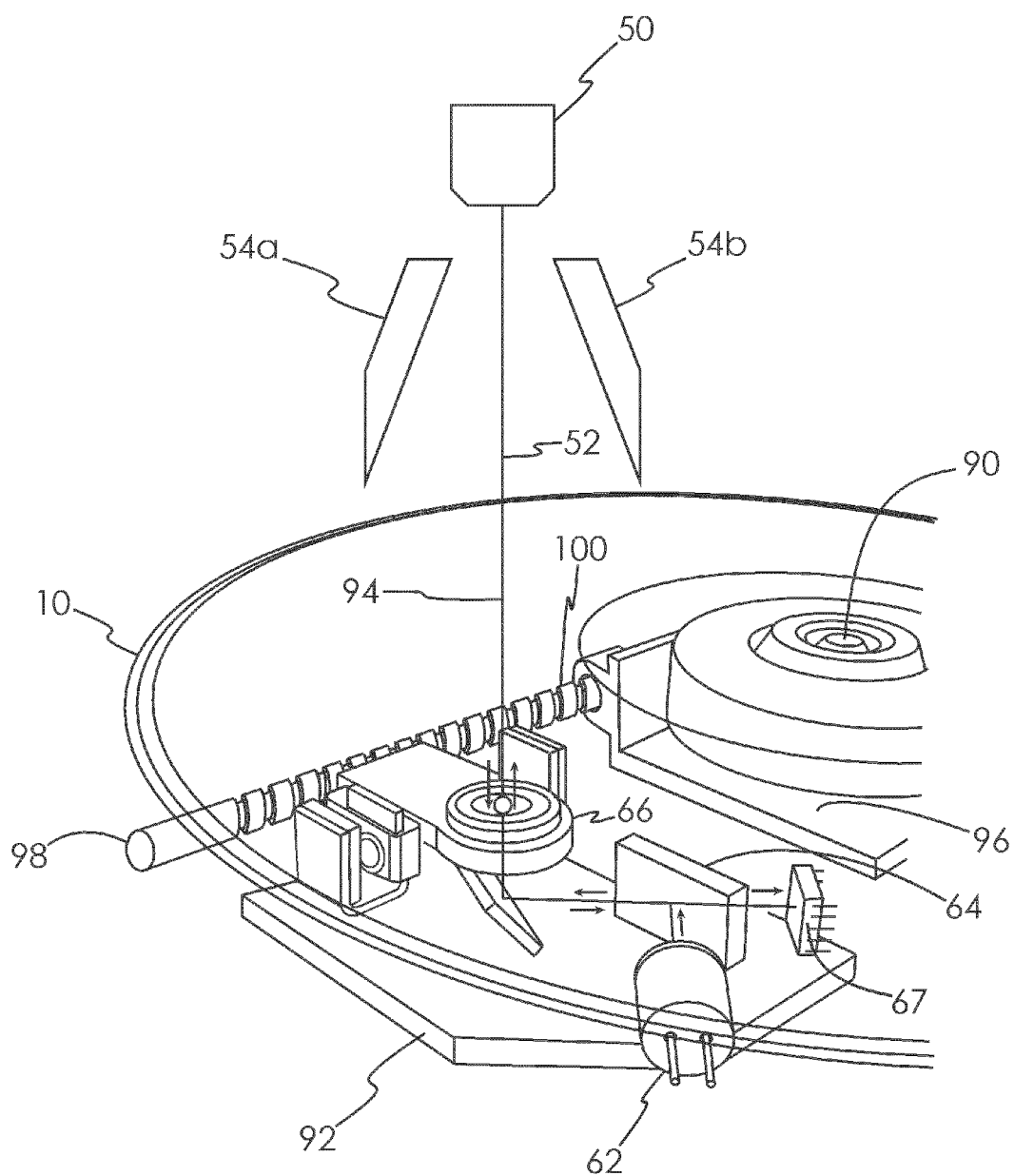
FIG. 6 is a schematic partial perspective view of an optical disc, optical disc drive and read/write head, and flow cytometry system according to one aspect of the present disclosure.

As discussed hereinabove, in some embodiments disclosed herein, the optical axis of the optical system is kept stationary and aligned with the jetting axis 52 of the cytometer 50, and the optical disc 10 is moved radially. This arrangement is illustrated in FIG. 6. A disc spin motor 90 attaches to the central hub of the disc 10 in order to rotate the disc 10. The optical components comprising the laser diode 62, beamsplitter prism 64, objective lens 66 and photodetector 67 reside on an optical system chassis 92 that is held in a fixed position with respect to the cytometer 50 so that the optical axis 94 is collinear with the cytometer 50 jetting axis 52. The motor 90 is mounted to a sled 96 that is translated horizontally by means of a stepping motor (not shown) that rotates a coarse pitch leadscrew 98 to move the sled 96 throughout its total travel range. The leadscrew 98 includes a helical groove 100 that engages a pin (not shown) on the sled 96.

Figure 7:
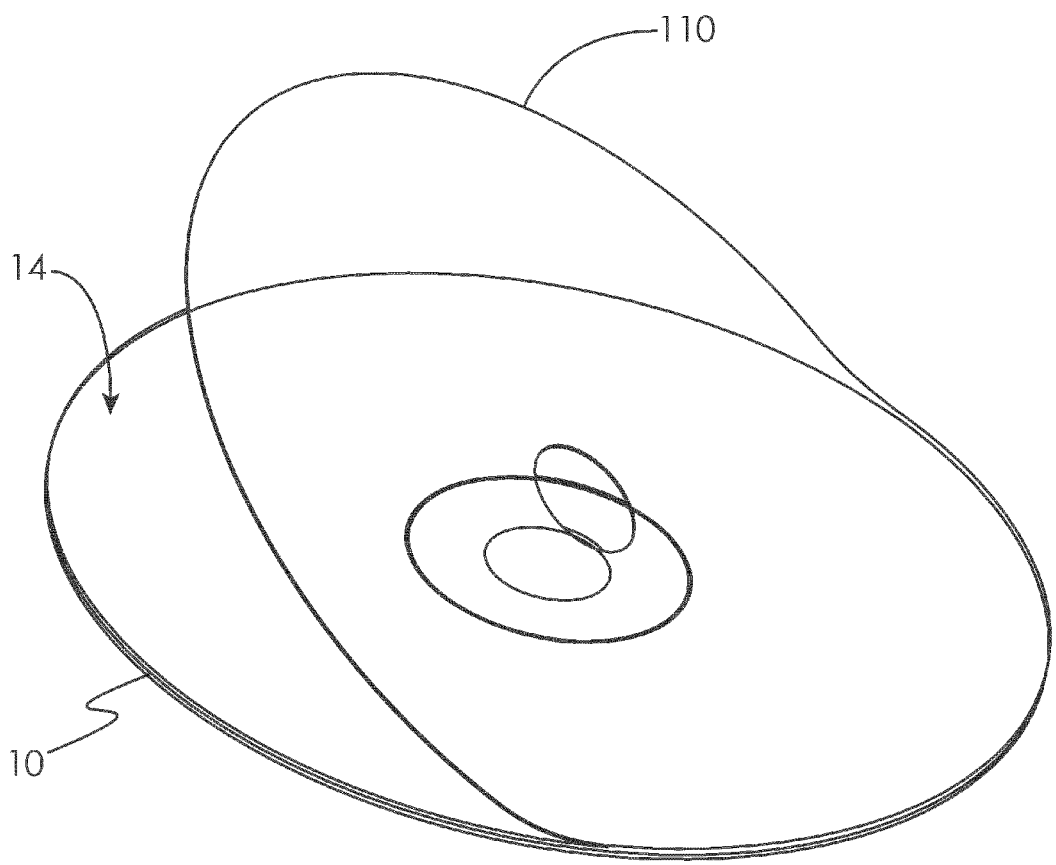
FIG. 7 is a perspective view of an optical disc and protective film cover according to one embodiment of the present disclosure.

Once the desired samples have been deposited on the disc 10, the samples may optionally be protected by covering the disc 10 with a protective film cover. As shown in FIG. 7, a film cover 110 may be placed over the deposition layer 14 and secured thereto. By way of non-limiting example, the protective cover 110 may be a 0.1 mm thick plastic, such as polycarbonate, film that is secured to the outer edge of disc 10 (such as by a pressure-sensitive adhesive (PSA) in some embodiments) to protect the samples deposited onto the deposition layer 14. Such film covering method may be accomplished by the rubber balloon press, roll press, or any other appropriate process.

It will be appreciated from the above disclosure that the sample deposition and data storage discs and methods disclosed herein allow for automated storage of high volumes of samples as they are measured, convenient later retrieval of and access to the samples and the accompanying measurement data. This allows the samples to be stored and then later observed in situ, transferred to another device, etc. Additionally, the samples can be processed on the disc 10 after deposition, such as by polymerase chain reaction, chemical reaction, or any other type of processing. The discs 10 will be useful in a broad range of analytic and laboratory procedures, including image microscopy, polymerase chain reaction, high-throughput drug discovery screening, and high-throughput DNA sequencing, to name just a few non-limiting examples. The discs 10 are additionally inexpensive to procure and to use, ecological, disposable and safe.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. It is also contemplated that structures and features embodied in the present examples can be altered, rearranged, substituted, deleted, duplicated, combined, or added to each other. The articles "the", "a" and "an" are not necessarily limited to mean only one, but rather are inclusive and open ended so as to include, optionally, multiple such elements.

What is claimed is:

1. A system, comprising:
    a flow cytometer having at least one droplet moving on a jetting axis;
    a deposition disc comprising a deposition layer and a recording layer;
    wherein the jetting axis intersects a portion of the deposition layer;
    a rotational drive system coupled to the deposition disc for controlling angular motion of the deposition disc;
    wherein the at least one droplet may be deposited by the flow cytometer onto the deposition layer;
    a first detection system including a first laser producing a first laser light focused on the recording layer of the deposition disc, the first detection system operative to determine a deposition position of the at least one droplet on the deposition layer; and
    a second detection system including a second laser producing a second laser light focused on the deposition layer, the second detection system operative to detect the deposition of the at least one droplet on the deposition layer;
    wherein the first detection system detects the deposition position of the at least one droplet and the second detection system detects the deposition of the at least one droplet substantially simultaneously.

2. The system of claim 1, further comprising:
    the deposition layer having a droplet deposition feature formed therein;
    wherein the at least one droplet may be deposited by the flow cytometer into the droplet deposition feature.

3. The system of claim 2, wherein said droplet deposition feature comprises a spiral groove.

4. The system of claim 2, wherein said droplet deposition feature comprises at least one radial groove.

5. The system of claim 1,
    wherein the recording layer is disposed on the deposition disc adjacent to the deposition layer, the recording layer comprising a laser guiding groove and a recording dye.

6. The system of claim 1, further comprising:
    a first beamsplitter;
    a dichroic mirror;
    a lens; and
    a first photodetector;
    wherein the first laser light from the first laser is reflected by the first beamsplitter, is reflected by the dichroic mirror, is focused on the recording layer by the lens, is reflected by the recording layer, is reflected by the dichroic mirror, and passes through the first beamsplitter to the first photodetector; and
    wherein the photodetector is operative to sense the first laser light to determine a deposition location of the at least one droplet on the deposition layer.

7. The system of claim 6, further comprising:
    a second beamsplitter; and
    a second photodetector, wherein the second laser light from the second laser passes through the second beamsplitter, passes through the dichroic mirror, is focused on the deposition layer by the lens, is reflected by the at least one droplet on the deposition layer, passes through the dichroic mirror, and is reflected by the second beamsplitter to the second photodetector; and
    wherein the second photodetector is operative to sense the second laser light to determine a landing of the at least one droplet on the deposition layer.

8. The system of claim 1, wherein the first laser comprises a 650 nm laser diode.

9. The system of claim 1, wherein the second laser comprises a 780 nm laser diode.

10. The system of claim 7, further comprising:
    a data processing device operatively coupled to the cytometer for receipt of measurement data therefrom, and operatively coupled to the first photodetector for receipt of address data therefrom and to the second photodetector for receipt of landing detection data therefrom;
    wherein the data processing device is operative to assemble a deposition data set comprising the measurement data and the address data.

11. The system of claim 10, wherein the data processing device is operatively coupled to the first laser and the first laser is operative to write the deposition data set to the recording layer.

12. The system of claim 10, wherein the measurement data comprises one or more measurement data types selected from the group consisting of: a fluorescence signal, a scatter signal, a fluorescence marker signal, a timing signal, and a droplet number.

13. The system of claim 1, wherein the rotational drive system is operational to rotate the deposition disc at a velocity selected from the group consisting of: a constant angular velocity and a constant linear velocity.

14. The system of claim 1, further comprising:
an optical system operative to read data from the deposition disc; and
a sled coupled to the rotational drive system;
wherein the optical system maintains a fixed position with respect to the jetting axis; and
wherein the sled is operative to translate the deposition disc and the rotational drive system with respect to the jetting axis.

15. The system of claim 14, further comprising:
a pin coupled to the sled;
a leadscrew having a helical groove that engages the pin; and
a stepper motor coupled to the leadscrew and operative to rotate the leadscrew.

16. The system of claim 1, further comprising a cover applied to the deposition layer.

17. The system of claim 16, wherein the cover comprises 0.1 mm thick polycarbonate film.

18. The system of claim 16, wherein the cover is applied to the deposition layer outer edge by a pressure-sensitive adhesive.

19. A system for use with a flow cytometer having at least one droplet moving on a jetting axis, the system comprising:
a deposition disc comprising:
a deposition layer; and
a recording layer;
wherein the deposition layer is positioned adjacent the recording layer;
wherein the jetting axis intersects a portion of the deposition layer; and
wherein the at least one droplet may be deposited by the flow cytometer onto the deposition layer;
a first detection system including a first laser producing first laser light focused on the recording layer;
a second detection system including a second laser producing second laser light focused on the deposition layer;
a first optical path operative to guide a first axis of the first laser light to be coextensive with the jetting axis;
a second optical path operative to guide a second axis of the second laser light to be coextensive with the jetting axis; and
a lens intersected by the jetting axis;
wherein the lens focuses the first laser light on the recording layer;
wherein the lens focuses the second laser light on the deposition layer;
wherein the first detection system is operative to detect first laser light reflected from the recording layer and the second detection system is operative to detect second laser light reflected from the deposition layer substantially simultaneously.

20. The system of claim 19, further comprising:
the deposition layer having a droplet deposition feature formed therein;
wherein the at least one droplet may be deposited by the flow cytometer into the droplet deposition feature.

21. The system of claim 19, further comprising:
a rotational drive system coupled to the deposition disc for controlling angular motion of the deposition disc.

22. The system of claim 19, wherein the lens has a first numerical aperture for the first laser light and a second numerical aperture for the second laser light.

23. The system of claim 19, wherein the first detection system and the second detection system are further operative to substantially simultaneously:
detect droplet deposition onto the deposition layer; and
read an address from the recording layer.

24. A method for detecting the deposition of at least one droplet of a flow cytometer on a deposition disc, wherein the deposition disc includes a deposition layer and a recording layer, the method comprising:
depositing the at least one droplet onto the deposition layer with the flow cytometer;
determining a deposition position of the at least one droplet on the deposition layer with a first detection system including a first laser producing a first laser light focused on the recording layer;
detecting the deposition of the at least one droplet on the deposition layer with a second detection system including a second laser producing a second laser light focused on the deposition layer; and
detecting the deposition position of the at least one droplet with the first detection system and detecting the deposition of the at least one droplet with the second detection system substantially simultaneously.

\* \* \* \* \*